United States Patent [19]

Brown

[11] Patent Number: 5,543,569
[45] Date of Patent: Aug. 6, 1996

[54] BORANE-N,N-DIALKYLANILINE HYDROBORATION AGENTS

[75] Inventor: Herbert C. Brown, West Lafayette, Ind.

[73] Assignee: Aldrich Chemical Company, Inc., Milwaukee, Wis.

[21] Appl. No.: 437,586

[22] Filed: May 9, 1995

[51] Int. Cl.$^6$ ............................................. C07F 5/02
[52] U.S. Cl. ............................................. 564/8; 564/9
[58] Field of Search ........................................ 564/8, 9

[56] References Cited

U.S. PATENT DOCUMENTS 4,271,317  6/1981  Pelter et al. ..................... 564/8

OTHER PUBLICATIONS

Brown et al, J. Am. Chem. Soc., 1984, 106, 1863–1865.
Kanth et al., J. Chem. Soc. Chem. Commun., 1145–1147, 1990.

*Primary Examiner*—Shailendra Kumar
*Attorney, Agent, or Firm*—Niblack & Niblack

[57] ABSTRACT

Borane-N,N-dialkylanilines represented by the formula

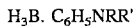

$H_3B \cdot C_6H_5NRR'$ wherein N is nitrogen, R is isobutyl or isopropyl and R' is straight or branched chain lower alkyl. The compounds are useful as hydroboration agents and for generating diborane.

15 Claims, No Drawings

BORANE-N,N-DIALKYLANILINE HYDROBORATION AGENTS

BACKGROUND OF THE INVENTION

A. Field of Invention

The present invention provides novel hydroboration agents and more particularly relates to a novel class of borane adducts with N,N-dialkylanilines.

B. Prior Art

Borane adducts with amines are versatile reagents exhibiting many different properties as compared to the metal borohydrides. For example, they are soluble in a variety of solvents, including hydrocarbons or even water, and in some cases can be used in an acidic medium. Many adducts have been synthesized. See for example, Long, L. H. in W. J. Mellor *A Comprehensive Treatise on Inorganic and Theoretical Chemistry*; Longman: London, 1981, Supplement Vol. 5, Part B1, p 1.; and Meller, A. In Gmelin *Handbook of Inorganic and Organometallic Chemistry*; Springer: Berlin, 1992, 4th Supplement, Vol. 3, p 1. Several are commercially available. They find various uses, e.g., as fuel additives, polymerization catalysts, polymer stabilizers and stain removers, in metal plating and in the dye and pharmaceutical industries. See Lane, C. F. *Aldrichimica Acta* 1973, 6, 51. Most of these applications are based on their reducing properties.

In contrast, the use of borane-amine adducts for hydroboration is rather limited due to strong complexation, which renders their reactivity low as compared to the weak borane adducts with ethers and sulfides. For example, borane-triethylamine does not hydroborate 1-octene at room temperature and only very slowly in refluxing tetrahydrofuran (THF). See Brown, H. C. et al. *Inorganic Chem.* 1984, 23, 2746.

Borane adducts with the less basic anilines are weaker and hence more reactive. See Brown, H. C. et al. *Inorganic Chem.* 1984, 23, 2746; Narayana, C. et al. Organometal. Chem. 1987, 23, 145; and Camacho, C. et al. *Synthesis* 1982, 1027. Borane-N,N-diethylaniline hydroborates 1-octene in tetrahydrofuran at room temperature in 2 hours. The adducts with N-phenylmorpholine and N-phenylaniline are still more reactive. However, they are air-sensitive solids which are considered less convenient to handle than liquids for large-scale commercial applications.

Borane-tetrahydrofuran is a valuable reagent for the hydroboration of olefins and for the reduction of organic compounds. It suffers from the disadvantage in that the solutions are unstable over a period of time. U.S. Pat. No. 3,882,037 discloses stabilized borane-tetrahydrofuran solutions which permit storage of such solutions for relatively longer periods of time. However, the inherent availability only as a relatively dilute solution in tetrahydrofuran poses a drawback to commercial use of this reagent.

Borane-methyl sulfide (BMS) is much more stable than borane-tetrahydrofuran and is widely used for both hydroboration and reduction [See Burg et al., *J. Am. Chem. Sec.* 76, 3307 (1954) and Coyle et al., *J. Am. Chem. Sec.* 81, 2989 (1959)]. However, it suffers from the serious disadvantage in that it yields a product which contains free dimethyl sulfide. The free dimethyl sulfide is highly volatile, b.p. 38° C., flammable and has a very noxious odor. Moreover, it is not soluble in water, so it cannot be disposed of by washing it away with water.

Borane-1,4-thioxane (U.S. Pat. No. 4,298,750) is another valuable hydroboration agent. It has both lower volatility and milder odor than dimethyl sulfide. It has a limited solubility in water and can be easily oxidized to the corresponding sulfoxide, which is miscible in water. This agent is a liquid, 8M in $BH_3$, stable over prolonged periods. Unfortunately, this commercially available reagent is relatively costly compared to borane-tetrahydrofuran and borane-dimethyl sulfide.

The growing importance of borane reagents for the synthesis of pharmaceuticals and other compounds and the problems associated with other well established borane adduct hydroboration agents, e.g., low concentration and stability, high volatility, flammability, unpleasant odor, as discussed above, create a need for easy to handle, stable and environmentally benign hydroborating agents as discussed specifically below. The present invention fulfills that need.

SUMMARY OF THE INVENTION

The borane-N,N-dialkylanilines of the present invention are represented by the formula $$H_3B \cdot NC_6H_5RR'$$

wherein N is nitrogen, R is isobutyl or isopropyl and R' is straight or branched chain lower alkyl. For the sake of brevity, the term "Ph" will be used herein as shorthand for phenyl or $C_6H_5$.

N,N-alkylisopropylanilines and N,N-alkylisobutylanilines are valuable new borane carriers, forming liquid borane adducts which are stable at room temperature, soluble in various solvents, and hydroborating 1-octene in THF in less than 1 hour at room temperature.

Representative compounds of the present invention include but are not limited to the borane adducts of: N,N-isopropylmethylaniline; N,N-isopropylethylaniline; N,N-isopropyl-n-propylaniline; N,N-diisopropylaniline; N,N-isobutylmethylaniline; N,N-isobutylethylaniline; N,N-isobutyl-n-propylaniline; and the like.

For ease of discussion, references numbers for the illustrative compounds discussed herein are set forth in Table 1.

TABLE 1

| Reference | Compound | R' | R |
|---|---|---|---|
| 1a | PhNBu$^i$Me | isobutyl | methyl |
| 1b | PhNBu$^i$Et | isobutyl | ethyl |
| 1c | PhNBu$^i$ | isobutyl | isobutyl |
| 1d | PhNBu$^i$Pr$^n$ | isobutyl | n-propyl |
| 2a | PhNPr$^i$Me | isopropyl | methyl |
| 2b | PhNPr$^i$Et | isopropyl | ethyl |
| 2c | PhNPr$^i$Pr$^n$ | isopropyl | n-propyl |
| 2d | PhNPr$^i_2$ | isopropyl | isopropyl |

It is surprising that the mixed amines of the present invention exhibit a wholly unexpected increase in performance over the previously reported diethylaniline. The borane adduct of diethylaniline require a 2 hours to hydroborates 1-octene in THF at 25° C. Unexpectedly, most of the compounds of this invention hydroborate 1-octene in THF in 15–30 minutes, a 400% or greater improvement. The mixed amines used in the practice of this invention to prepare the novel borane adducts were largely prepared from low cost aniline, N-methylaniline and N-ethylaniline. All three are manufactured on a large scale for the dye industry. The general preparation of the amines is represented by reaction scheme I.

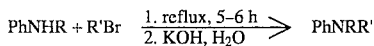

PhNHR + R'Br $\xrightarrow[\text{2. KOH, H}_2\text{O}]{\text{1. reflux, 5-6 h}}$ PhNRR'  (I)

1a: R = Me, R' = i-Bu; 2a: R = Me, R' = i-Pr
1b: R = Et, R' = i-Bu; 2b: R = Et, R' = i-Pr

An alternate procedure for preparing amines useful in the practice of this invention is from aniline comprising either reductive alkylation of an intermediate N-isopropylaniline, or stepwise alkylation according to reaction scheme II.

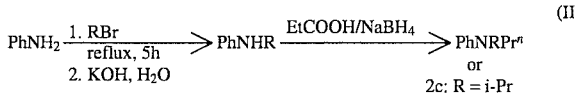

PhNH$_2$ $\xrightarrow[\text{2. KOH, H}_2\text{O}]{\text{1. RBr, reflux, 5h}}$ PhNHR $\xrightarrow{\text{EtCOOH/NaBH}_4}$ PhNRPr$^n$ or 2c: R = i-Pr

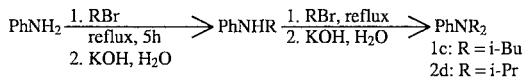

PhNH$_2$ $\xrightarrow[\text{2. KOH, H}_2\text{O}]{\text{1. RBr, reflux, 5h}}$ PhNHR $\xrightarrow[\text{2. KOH, H}_2\text{O}]{\text{1. RBr, reflux}}$ PhNR$_2$
1c: R = i-Bu
2d: R = i-Pr The alkylation of N-isobutylaniline with isobutyl bromide is very slow. The reaction rate is accelerated in the presence of tetrabutylammonium iodide and the product can be obtained in a shorter time and higher yield. Similarly, diisopropylaniline can be prepared by stepwise alkylation of aniline with isopropyl bromide. The most straight forward method of preparing the desired starting material is to heat the aniline base with RX, preferably the bromide. A typical synthesis is represented by the reaction scheme III.

2PhNHEt+Pr$^i$Br→PhNEtPr$^i$+PhNEtH$_2$+Br  (III)

In the above reaction, the additional mole of the aniline base reacts with the hydrogen bromide by-product. Addition of one mole of sodium hydroxide to the product yields the two amines PhNEtPr$^i$+PhNEtH plus sodium bromide and water. The two amines are readily distilled to separate PhNEtH and the desired product PhNEtPr$^i$. PhNEtH is returned to the process.

After the amines were made, they were placed into a flask containing a magnetic stirring bar, an inlet for a hypodermic needle, a mercury bubbler leading into a large test tube containing an 8 mm glass tub leading into a pool of mercury and an inlet for a hypodermic needle. A nitrogen or argon atmosphere was maintained. In the practice of the invention, diborane was generated by treating a 2M solution of sodium borohydride with an equivalent amount of boron-trifluoride-triglyme. Diborane is readily generated as represented by reaction scheme IV.

3NaBH$_4$+4BF$_3$.TG→2B$_2$H$_6$+3NaBF$_4$  (IV)

The NaBF$_4$ is soluble in diglyme or triglyme. The diborane (=2 BH$_3$) is passed into the desired aniline base (i.e. compounds 1 a-c or 2 a-d) being maintained at 0° C. with an external ice bath. The diborane is readily absorbed in most cases to give the borane addition compounds of the invention. This process is represented by reaction scheme V.

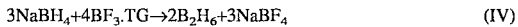

2PhNRR'+B$_2$H$_6$→2H$_3$B. NPhRR'  (V)

Following the reaction, a minute sample was removed with a hypodermic syringe and passed into the standard hydrolyzing mixture. In most cases, a quantitative yield was obtained. In those cases where the diborane was not absorbed quantitatively, such as when both R and R' are isobutyl, the diborane not absorbed passed through the bubbler into the tube containing a pool of mercury covered by sufficient tetrahydrofuran to absorb the diborane generated. At this point, a sample was also removed and analyzed for dissolved diborane by hydrolysis.

The flask containing the borane adduct was allowed to warm to room temperature. The escape of diborane through the bubbler was noted. Then both the borane-amine and the borane-THF products were examined for borane content by removing small samples and analyzing them by hydrolysis.

The molarity of the borane in the amine was noted. In general, with rare exceptions, such as when R and R' are isobutyl, the content represents a quantitative transfer. A sample of each representative compound prepared was then transferred to the NMR tube and the $^{11}$B spectrum determined.

A sample of the borane-amine was then mixed with 3 equivalents of 1-octene and the time noted for complete conversion to n-octylborane. Reaction scheme VI represents the later steps.

3HexCH=CH$_2$+H$_3$B. NPhRR'→n-Oct$_3$B+PhNRR'  (VI)

Oxidation with alkaline hydrogen peroxide, a quantitative reaction, gives 94% 1-octanol and 6% of 2-octanol.

A sample of the amine was also mixed with an equal number of moles of borane-methyl sulfide. The $^{11}$B spectrum revealed the formation of an equilibrium mixture of two compounds represented in reaction scheme (VII).

H$_3$B.SMe$_2$+PhNRR'⇌H$_3$B.SMe$_2$+H$_3$BNPhRR'+PhNRR'  (VII)

Table 4, which follows the examples, shows the percentage of each component at equilibrium for representative compounds disclosed and claimed herein.

The adducts of this invention are too unstable to distill. On heating, they lose diborane. However, the $^{11}$B spectra established that 1 mole of borane (BH$_3$) is absorbed per mole of amine, with the exceptions indicated.

The compounds were also prepared independently by equilibrating with borane-methyl sulfide and with borane-tetrahydrofuran. Analysis of samples by hydrolysis established the presence of a 1:1 combination of the amine and the borane. Finally, each mole of borane-amine, with rare exceptions as indicated, hydroborated 3 moles of 1-octene.

Hydroboration of internal olefins such as 3-hexene, cyclopentene, cyclohexene, cyclooctene, and norbornene all react quantitatively in the ratio shown in reaction scheme VIII.

3Olefin+H$_3$B-NPhRR'→R$_3$B+PhNRR'  (VIII)

Hydroboration of trisubstituted olefins, such as 2-methyl-2-butene, 1-methylcyclohexene, α-pinene, etc. proceeds in the ratio shown in reaction scheme IX.

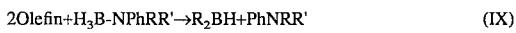

2Olefin+H$_3$B-NPhRR'→R$_2$BH+PhNRR'  (IX)

Hydroboration of more hindered alkenes, such as 2,3-dimethyl-2-butene and 2,4,4-trimethyl-2-pentene proceeds in a ratio of 1 alkene/H$_3$B-NPhRR'. In these cases, the products are RBH$_2$ and PhNRR'.

In all cases, the hydroboration of alkenes parallels the earlier hydroborations of representative alkenes as described in the literature for borane-tetrahydrofuran and borane-dimethylsulfide. Thus the present invention provides hydroboration reagents which are as effective as the known agents but which do not suffer from any of their drawbacks.

In another embodiment, the compounds of this invention are useful for generating diborane. The easy loss of diborane by heating is a valuable property for the compounds of this invention. It is difficult to ship diborane in cylinders under pressure. At room temperature, the metal in the cylinder catalyzes a decomposition of diborane into hydrogen and higher hydrides of boron. Under one embodiment of the invention, diborane can be readily generated by placing a compound of the invention into a reaction vessel and gradually raising the temperature to ~100° C. to produce a quantitative yield of diborane. The quantitative evolution of the gas is facilitated by using a slow stream of nitrogen or argon to carry the diborane out of the reaction vessel. Alternatively, a minor amount of an inert, volatile material, such as cyclohexane or toluene, can be added to the reaction vessel with a condenser used to minimize loss of the inert component. The generation of diborane in the above manner is represented by reaction scheme X.

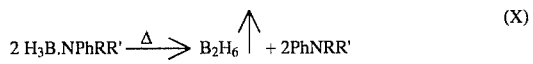

$$2 H_3B \cdot NPhRR' \xrightarrow{\Delta} B_2H_6 \uparrow + 2PhNRR' \quad (X)$$

The complexing ability of the amines toward borane was tested by the exchange of BMS (borane-methylsulfide) and $BH_3$. THF (borane- tetrahydrofuran) mixed in 1:1 molar ratio. The amount of borane taken by an amine in the equilibrium was determined by $^{11}B$ NMR and is shown in Tables 2, 3 and 4. Values for the exchange with borane-tetrahydrofuran, a 1M solution, should be considered less quantitative since THF is in large excess.

The borane adducts of this invention are highly reactive, hydroborating 1-octene is tetrahydrofuran at room temperature in less than 1 hour. A number of the adducts are liquids above 0° C. The preparation of representative borane-amine adducts of this invention are illustrated in the following examples.

DETAILED DESCRIPTION OF PREFERRED EMBODIMENTS

The following examples more fully illustrate the present invention.

EXAMPLE 1

N,N-Ethylisopropylaniline

In a 500 ml round-bottom flask filled with a magnetic stirrer and a reflux condenser was placed N-ethylaniline (52.4 g, 400 mmole) and 2-bromopropane (24.6 g, 200 mmol). The mixture was heated under reflux until the temperature increased to ~140° C. (~20 h). After cooling to room temperature, aqueous 5M potassium hydroxide solution (50 ml, 200 mmol) was added, the organic layer was separated and the aqueous layer was extracted with diethyl ether (2×25 ml). The extracts were combined with the organic layer and dried over magnesium sulfate. Ether was removed to give a fore-fraction of N-ethylaniline, followed by the product N,N-ethylisopropylaniline, bp 48° C./0.1 mm Hg, 27.5 g (84% yield).

EXAMPLE 2

N,N-Diisopropylaniline

A mixture of aniline (20.48 g, 0.22 mol) and 2-bromopropane (24.60 g, 0.2 mol) was refluxed until the temperature increased to 150° C. (5 h). After cooling to room temperature, aqueous 5M potassium hydroxide solution (50 ml, 0.25 mol) was added, the organic layer was separated and the aqueous layer was extracted with diethyl ether (2×25 ml). The extracts were combined with the organic layer and dried over magnesium sulfate. Ether was removed to give 27.15 g of a crude product. GC analysis on a 12 ft×0.125 inch column packed with 10% SE-30 on Chromosorb W 100–120 mesh, showed aniline (7%), N-isopropylaniline (89%) and N,N-diisopropylaniline (4%). 2-Bromopropane (26.60 g, 0.2 mol) was added and the mixture was refluxed until the temperature increased to 130° C. (~40 h). The workup described above was repeated and fractional distillation gave 31.15 g (88%) of product containing ~2% of N-isopropylaniline, which was removed by the addition of 2.5M n-butyllithium in hexane (5 ml) and distillation. There was obtained 28.67 g (81%) of the title product, bp 50–52° C./0.1 mm Hg, >99% GC pure.

EXAMPLE 3

N,N-Isopropyl-n-propylaniline

Sodium borohydride (12.86 g, 0.34 mol) was added in portions to a mixture of propionic acid (16.23 g, 0.22 mol) and N-isopropylaniline (10.00 g, 0.74 mol) at room temperature under nitrogen and the mixture was maintained at 55° C. for 1 h. Aqueous 5M potassium hydroxide solution (50 ml, 0.25 mol) was added, the organic layer was separated and the aqueous layer was extracted with diethyl ether (2×20 ml). The extracts were combined with the organic layer and dried over magnesium sulfate. The product was isolated by distillation, 9.73 g (74%), bp 88–89° C./5 mm Hg.

EXAMPLE 4

N,N-Diisobutylaniline

A mixture of aniline (14.90g, 0.16 mol), 1-bromo-2-methylpropane (21.92g, 0.16 mol) and tetrabutylammonium iodide (2.95g, 0.008 mol) was refluxed for 2.5 h. Aqueous 50% potassium hydroxide solution (33.66g, 0.3 mol) was added, the organic layer was separated and dried over magnesium sulfate. The crude product was further treated with 1-bromo-2-methylpropane (21.92 g, 0.16 mol) and tetrabutylammonium iodide (2.95 g) and refluxed for 5.5 h. The mixture was worked up as described above. GC analysis showed N-isobutylaniline (63%) and N,N-diisobutylaniline (37%). The mixture was treated with the same amounts of 1-bromo-2-methylpropane and tetrabutylammonium iodide as above, refluxed for 8 h. Basic workup as described above and fractional distillation gave the title compound, 20.90 g (64%), bp 86–87° C./1.5 mm Hg.

The properties of representative compounds 1a-c and 2a-d are set forth in Table 2.

TABLE 2

| | Representative N,N-Dialkylanilines | | | | |
|---|---|---|---|---|---|
| Amine | Yield[a] (%) | bp (°C.)/ mm Hg | Molecular Formula or Lit. bp (°C.)/Torr | $^1$H NMR (CDCl$_3$/TMS)[b] δ, J (Hz) | MS (70 eV)[c] m/z (%) |
| PhNBu$^i$Me | 85 | 68/12 | 115/14[16] | 0.90(d, 6H, J=6.6, CH$_3$), 2.05(nonet 1H, J=6.8, CH), 2.91 (s, 3H, CH$_3$), 3.1(d, 2H, J=7.2, CH$_2$), 6.65(t, 1H, J=6.3, H$_p$Ph), 6.68 (d, 2H, J=8.0, H$_o$Ph), 7.31(d, 2H, J=8.4, H$_m$Ph) | 163(M$^+$, 11) 120(100) 77(17) |
| PhNBu$^i$Et | 79 | 44/0.1 | 228–231/770[17] | 0.92(d, 6H, J=6.6, CH$_3$), 1.11(t, | 177(M$^+$, 14), |

TABLE 2-continued

Representative N,N-Dialkylanilines

| Amine | Yield[a] (%) | bp (°C.)/ mm Hg | Molecular Formula or Lit. bp (°C.)/Torr | $^1$H NMR (CDCl$_3$/TMS)[b] δ, J (Hz) | MS (70 eV)[c] m/z (%) |
|---|---|---|---|---|---|
| | | | | 3H, J=7.08, CH$_3$), 2.03(nonet, 1H, J=7.0, CH), 3.0(d, 2H, J=7.3, CH$_2$), 3.3(q, 2H, J=7.0, CH$_2$), 6.60 (t, 1H, J=7.2, H$_p$Ph), 6.66(d, 2H, J=8.1, H$_o$Ph), 6.87(d, 2H, J=7.2, H$_m$Ph) | 134(100), 106(28), 77(22) |
| PhNBu$^i_2$ | 52 | 86/1.5 | 142–144/21[11] | 0.89(d, 12H, J=6.6, CH$_3$), 2.08(nonet, 2H, J=6.6, CH), 3.13(d, 4H, J=7.2, CH$_2$), 6.61(t, 1H, J=6.31, H$_p$Ph), 6.64(d, 2H, J=8.0, H$_o$Ph) 7.18(d, 2H, J=9.9, H$_m$Ph) | 205(M$^+$, 15), 162(100), 120 (42), 106(92), 77(16), 57(17) |
| PhNPr$^i$Me | 79 | 46/0.5 | 215–228/760[18] 82–89/14[18] | 1.41(d, 6H, J=6.6, CH$_3$), 2.72(s, 3H, CH$_3$), 4.08(sep., 1H, J=6.6, CH), 6.68(t, 1H, J=7.2, H$_p$Ph), 6.78(d, 2H, J=8.7, H$_o$Ph), 7.22(d, 2H, J=7.2, H$_m$Ph) | 149(M$^+$, 17) 134(100), 77(21) |
| PhNPr$^i$Et | 84 | 48/0.1 | 223–225/760[18] 100–102/13[18] | 1.16(t, 3H, J=6.9, CH$_3$), 1.18(d, 6H, J=6.6, CH$_3$), 3.23(q, 2H, J=6.9, CH$_2$), 4.04(sep., 1H, J= 6.5, CH), 6.65(t, 1H, J=7.1, H$_p$Ph), 6.74(d, 2H, J=8.2, H$_o$Ph), 7.21(d, 2H, j=6.0, H$_m$Ph) | 163(M$^+$, 22) 148(100), 120 (22), 77(22) |
| PhNPr$^i$Pr$^n$ | 74 | 88/5 | C$_{12}$H$_{19}$N[d] (177.29) | 0.90(t, 3H, J=7.4, CH$_3$), 1.16(d, 6H, J=6.6, CH$_3$), 1.58(quint, 2H, J=7.1, CH$_2$), 3.05(t, 2H, J=7.8, CH$_2$), 4.03(sep., 1H, J=6.6, CH), 6.63(t, 1H, J=7.2, H$_p$Ph), 6.70(d, 2H, J=8.5, H$_p$Ph), 7.21 (d, 2H, J=8.8, H$_m$Ph) | 177(M$^+$, 20) 162(54), 148(64), 120 (30), 106 (100), 77(31) |
| PhNPr$^i_2$ | 81 | 50–52/0.1 | 225–227/760[18] 98–100/13[18] | 1.20(d, 12H, J=6.7, CH$_3$), 3.78 (sep., 2H, J=6.7, CH), 6.75(t, 1H, J=6.4, H$_o$Ph), 6.89(d, 2H, J=6.5, H$_o$Ph), 7.20(d, 2H, J=6.6, H$_m$Ph) | 177(M$^+$, 12) 162(78), 120 (100), 77(22) |

[a]Isolated.
[b]Recorded on a Varian Gemini 300 multinuclear spectrometer.
[c]Recorded on a 4000 Finnigan MAT spectrometer, EI, CI.
[d]Calcd. 81.30% C; 10.79% H; 7.90% N. Obtnd. 80.95% C; 11.04% H; 8.28% N.

The $^{13}$C NMR Spectral Data of the representative N,N-dialkylanilines characterized in Table 1 are set forth in Table 3.

TABLE 3

$^{13}$C NMR Spectral Data of Compounds 1a–c and 2a–d (Cut and Paste MAC 11 Table 2)
$^{13}$C NMR (CDCl$_3$/TMS),[a] δ

| Amine | Alkyl | | | Isobutyl | | | | Isopropyl | | | Aromatic Signals | | |
|---|---|---|---|---|---|---|---|---|---|---|---|---|---|
| | C$_1$ | C$_2$ | C$_3$ | C$_1$ | C$_2$ | Me | Me | C$_1$ | Me | Me | Ipso | Ortho | Meta | Para |
| 1a | 39.35 | — | — | 60.37 | 26.29 | 20.38 | 20.38 | — | — | — | 148.16 | 112.38 | 128.96 | 115.05 |
| 1b | 45.76 | 11.57 | — | 58.49 | 27.22 | 20.40 | 20.40 | — | — | — | 148.29 | 111.97 | 129.10 | 115.19 |
| 1c | — | — | — | 60.40 | 26.32 | 20.41 | 20.41 | — | — | — | 148.22 | 112.42 | 128.99 | 115.08 |
| 2a | 29.71 | — | — | — | — | — | — | 48.87 | 19.27 | 19.27 | 150.19 | 113.31 | 129.00 | 116.40 |
| 2b | 37.90 | 15.08 | — | — | — | — | — | 48.13 | 20.07 | 20.07 | 148.51 | 112.89 | 129.17 | 115.78 |
| 2c | 45.80 | 22.46 | 11.41 | — | — | — | — | 48.40 | 20.04 | 20.04 | 146.00 | 113.14 | 129.12 | 115.87 |
| 2d | — | — | — | — | — | — | — | 47.55 | 21.35 | 21.35 | 148.03 | 118.29 | 128.39 | 119.49 |

[a]Recorded on a Varian Gemini 300 multinuclear spectrometer.

EXAMPLE 5

Generation of Diborane

A 50-ml one-neck, round-bottom flask provided with a septum inlet, magnetic stirring bar and an adapter with a stopcock was charged with boron trifluoride-diglyme or -triglyme adduct (75 mmol). A 2M solution of sodium borohydride in triglyme (28.5 ml, 57 mmol) was added dropwise by means of a hypodermic syringe. Generation of diborane is smooth and the reaction is not exothermic. After the addition was completed, the flask was heated to 100° C. and kept at this temperature for 15 min. Diborane was absorbed in tetrahydrofuran (30 ml) at 0° C. Analysis of the BH3.THF solution obtained for active hydride by hydrolysis according to a standard procedure described in Brown, H. C. *Organic Syntheses via Boranes*; J. Wiley: New York, 1975, p. 241. showed 2.37M concentration of borane (95% yield); $^{11}$B NMR, δ, +1.0 ppm

EXAMPLE 6

General Procedure for Preparation of Borane-N,N-Dialkylaniline Adducts

Diborane (Example 5) was passed into a neat amine (50 mmol) at 0° C., contained in a flask fitted with a sintered glass inlet, a magnetic stirring bar and an exit bubbler. Excess diborane not absorbed by the amine passed through the mercury in the bubbler and dissolved in the next bubbler containing tetrahydrofuran (10 ml) overlaying the mercury, cooled in ice water. A second mercury bubbler was placed in series with the bubbler containing the tetrahydrofuran. Inlet tubes fitted with rubber serum caps were fitted to the flask containing the amine and to the bubbler containing the mercury overlaid with THF so that small samples of the borane-amine and the THF solution containing excess diborane can be removed by hypodermic syringes for analysis without opening the system to the atmosphere. The entire apparatus was flushed with nitrogen or argon and maintained under an inert atmosphere until the preparation of the borane-N,N-dialkylaniline adduct had been completed and the product had been transferred to a suitable storage flask under an inert atmosphere.

Diborane was passed into the amine until the concentration of excess borane in the THF was ~1M. A small sample of the amine-borane adduct was removed with a hypodermic syringe and analyzed. Then the flask containing the borane adduct was allowed to stand at room temperature and liberation of diborane, if any, noted on the bubbler. Small samples of the borane-amine and the THF solution above the bubbler were removed with syringes and analyzed for active hydrogen using a 2M hydrochloric acid-glycerol-water (2:1:1) hydrolysis solution. This provided information to calculate the molarity of the borane-amine formed at 0° C. and at 25° C. A sample of the amine-borane was placed in an NMR tube and the $^{11}$B spectrum determined.

EXAMPLE 7

Borane-N,N-Isopropylmethylaniline

In the flask of the apparatus described in Example 6 was placed 50 mmol of N,N-isopropylmethylaniline. The flask was cooled to 0° C. by immersion in an ice bath. The apparatus was flushed with nitrogen or argon and an inert atmosphere maintained. Diborane, generated as described in Example 5, was passed into the amine until no more was being dissolved. Removal of a small sample of the liquid product with a hypodermic syringe indicated the molarity of the borane in the amine was 4.9. The flask was allowed to warm to room temperature overnight. Only trace amounts of diborane passed through the bubbler. At room temperature, a second aliquot was removed and analyzed. The molarity of the borane was the same: 4.9. The borane and amine were in a ratio of 1:1. A sample of the amine-borane was placed in an NMR tube and the $^{11}$B NMR spectrum determined. Only one boron component was present with δ=−8.77 Hertz (Hz).

A 10-mmol sample of the borane-N,N-isopropylmethylaniline was added to the THF containing 30 mmol of 1-octene and the reaction followed by $^{11}$B NMR. In 30 minutes, the peak at δ=18.77 Hz had disappeared and the broad peak characteristic of n-octyl$_3$B had appeared.

EXAMPLE 8

Borane-N,N-Isopropylethylaniline

The apparatus described in Example 6 was assembled, flushed with nitrogen and a nitrogen atmosphere maintained throughout the experiment. In the flask was placed 50 mmol of N,N-isopropylmethylaniline. The flask was cooled to 0° C. by immersion in an ice-bath. The apparatus was flushed with nitrogen or argon and an inert atmosphere maintained. Diborane was passed in until the amine was saturated. An analysis of a small sample showed the borane content to be 4.7M with a ratio of borane to amine of 1:1. The $^{11}$B peak is at −14.68 Hertz. The product, 10 mmol of borane-N,N-isopropylethylaniline, was added to 30 mmol of 1-octene in 30 ml of THF solution. In 15 minutes the peak at −14.68 Hertz had vanished and the broad peak characteristic of n-octyl$_3$B had appeared.

EXAMPLE 9

Borane-N,N-Isopropyl-n-propylaniline

The procedure described in Examples 6, 7 and 8 was followed for the preparation of borane-N,N-isopropyl-n-propylaniline. The product is a liquid and stable, both at 0° C. and 25° C. It exhibits an $^{11}$B NMR at −14.21 Hertz. It hydroborates 3 mmol of 1-octene completely in 15 min.

EXAMPLE 10

Borane-N,N-Diisopropylaniline

The procedure described in the above examples was followed. The diisopropylaniline at first absorbed diborane, but then a crystalline solid formed and absorption of the diborane could not be completed. By adding borane-tetrahydrofuran to the amine, the crystalline solid could be prepared with a 1:1 ratio of borane:amine. The solid exhibited an mp of 36–38° C. The $^{11}$B NMR spectrum in THF revealed a single peak at δ–6.49 Hertz. In THF, hydroboration of 1-octene was fast and quantitative in 15 min, forming n-octyl$_3$B.

EXAMPLE 11

Borane-N,N-Isobutylmethylaniline

An identical procedure to that described in Examples 6–9 was followed. In this case, the product, borane-N,N-isobutylmethylaniline, was readily formed as a liquid with the two components present in a 1:1 ratio. The molarity of the neat product is 4.5M. The $^{11}$B peak is at δ–3.26 Hertz. Hydroboration of 1-octene in THF proceeded quantitatively in 15 min.

EXAMPLE 12

Borane-N,N-Isobutylethylaniline

The title compound was prepared following the identical procedure to that described in Examples 6–9. In this case also the product is a liquid, but a new phenomenon appears. the product exhibits a molarity of 4.0M at 0° C. But on warming to 25°, slow loss of some diborane through the bubbler is observed In 4 days, the molarity had dropped to 3.2M, with further loss of diborane becoming very slow. The $^{11}$B spectrum showed a peak at δ−9.17 Hertz. The hydroboration of 1-octene was complete at 25° C. in 15 min.

EXAMPLE 13

Borane-N,N-Diisobutylaniline

The procedure described in the above examples was identical, but only minor amounts of diborane was absorbed by the amine. At 0° C. the molarity was only 0.9M. On warming to room temperature, some of this low concentration was lost through the bubbler and the molarity dropped to 0.6M in 24 h. The $^{11}$B peak appeared at the usual place for the borane-amine: δ=−9.68 Hertz. Hydroboration of 1-octene was very fast, as expected for such an unstable complex, but this compound was not as satisfactory as the other borane-amine adducts disclosed herein.

EXAMPLE 14

Hydroboration of Representative Olefins with Borane-N,N-dialkylamine Adducts In a suitably sized reaction vessel cooled to 0° C. is placed one mole of the borane-N,N-dialkylamine adduct either neat or in a suitable solvent (such as ethyl ether, tetrahydrofuran, methylene chloride, monoglyme, toluene or dioxane). To the reagent are added 3 moles of a terminal olefin, such as 1-octene, 1-dodecene, 1-vinylcyclohexene, 2-methyl-1-butene, α-methylstyrene, etc., at such a rate that the temperature does not go significantly above room temperature. In all cases, the corresponding organoboranes, R$_3$B, are formed. Careful addition of one mole of 3M sodium hydroxide with 3 moles of 30% (10M) hydrogen peroxide at such a rate that the temperature does not go above 50° C. provides an essentially quantitative yield of three moles of the alcohol, ROH. Ether is added to the reaction mixture, followed by 1.0 mole of 6M HCl. The amine base goes into the aqueous layer. The alcohol is in the ether layer. The ether layer is separated, dried over magnesium sulfate and distilled to give an essentially quantitative yield of the alcohol, ROH. Addition of 1.1 mole of 3M sodium hydroxide liberates the amine. Extraction in ether and drying over magnesium sulfate gives an essentially quantitative recovery of the amine PhNRR'.

The complexing ability of the borane-N,N-dialkylaniline adducts disclosed and claimed herein was tested by exchange with BMS and BH$_3$. THF. The amount of borane taken by the compounds of the invention in the equilibrium is shown Table 4 along with the Exchange %, $^{11}$B NMR and other data. As can be seen by the data, the N,N-alkylisopropyl- and N,N-alkylisobutylanilines are valuable new borane carriers which meet the desired criteria of forming liquid borane adducts which are stable at room temperature, soluble in various solvents, and which hydroborate 1-octene in THF in less than 1 hour at room temperature.

TABLE 4

| | Borane-N,N-Dialkylaniline Adducts | | | | | | |
|---|---|---|---|---|---|---|---|
| | Exchange,[a] % | | Amine.BH$_3$ | | | Hydroboration of | |
| | | | State[b] | | $^{11}$B NMR[d] | 1-octene,[e] rt | |
| Amine | BH$_3$.SMe$_2$ | BH$_3$.THF | (mp, °C.) | [BH$_3$][c] | δ[f] | in THF[g] | Neat |
| PhNEt$_2$ | 66 | 94 | liquid | 4.8 | −11.55 | 2 h[h] | 12 h |
| 1a | 30 | 80 | liquid | 4.5 | −3.26 | 30 min | 2 h |
| 1b | 19 | 61 | liquid | 4.0→3.2[i] | −9.17 | 15 min | 1 h |
| 1c | 0 | 10 | liquid | 0.9→0.6[i] | −9.68[k] | 15 min | — |
| 2a | 50 | 85 | liquid | 4.9 | −8.77 | 30 min | 12 h |
| 2b | 36 | 79 | liquid | 4.7 | −14.68 | 15 min | 2 h |
| 2c | 25 | 70 | liquid | 4.1 | −14.21 | 15 min | 2 h |
| 2d | 0 | 36 | solid (36–38) | — | −16.49[k] | 15 min | 45 min[l] |

[a]Amine mixed with BMS or BH$_3$.THF in 1:1 molar ratio and analyzed by $^{11}$B NMR.
[b]At 0° C.
[c]Estimated by hydrolysis in 2 M HCl-glycerol-water (2:1:1) and measuring hydrogen evolved.
[d]Recorded on a Varian Gemini 300 multinuclear spectrometer.
[e]5% excess of 1-octene.
[f]From the exchange with BMS.
[g]3 M solution in 1-octene.
[h]Ref 6.
[i]Loss of borane in 4 days at room temperature.
[j]Loss of borane in 24 h at room temperature.
[k]From the exchange with BH$_3$.THF.
[l]3 M solution of the adduct in 2d.

In addition to their value as hydroborating agents, the claimed compounds are useful in the generation of diborane according the the general method described in Example 16.

EXAMPLE 16

Alternate Method of Generating Diborane

Diborane is readily generated by placing a compound of the invention into a reaction vessel and gradually raising the temperature to ~100° C. to produce a quantitative yield of diborane. The quantitative evolution of the gas is facilitated by using a slow stream of nitrogen or argon to carry the diborane out of the reaction vessel.

The invention claimed is:

1. Borane-N,N-dialkylanilines represented by the formula $H_3B \cdot C_6H_5NRR'$ wherein N is nitrogen, R is isobutyl or isopropyl and R' is straight or branched chain lower alkyl.

2. A borane-N,N-dialkylaniline of claim 1 wherein R is isopropyl.

3. A compound of claim 2, borane-N,N-isopropylmethylaniline.

4. A compound of claim 2, borane-N,N-isopropylethylaniline.

5. A compound of claim 2, borane-N,N-isopropyl-n-propylaniline.

6. A compound of claim 2, borane-N,N-diisopropylaniline.

7. A compound of claim 2, borane-N,N-isopropyl-n-butylaniline.

8. A compound of claim 2, borane-N,N-isopropyl-n-pentylaniline.

9. A compound of claim 1 wherein R is isobutyl.

10. A compound of claim 9, borane-N,N-isobutylmethylaniline.

11. A compound of claim 9, borane-N,N-isobutylethylaniline.

12. A compound of claim 9, borane-N,N-isobutyl-n-propylaniline.

13. A compound of claim 9, borane-N,N-isobutylisopropylaniline.

14. A compound of claim 9, borane-N,N-isobutyl-n-butylaniline.

15. A compound of claim 9, borane-N,N-isobutyl-n-pentylaniline.

* * * * *